United States Patent [19]

Binder et al.

[11] Patent Number: 4,841,065
[45] Date of Patent: Jun. 20, 1989

[54] ISOXAZOLE DERIVATIVES WITH ANTIVIRAL ACTIVITIES AND PHARMACEUTICAL PRODUCTS CONTAINING THESE

[75] Inventors: Dieter Binder, Vienna; Franz Rovenszky, Bruck an der Leitha; Hubert P. Ferber, Ansfelden, all of Austria

[73] Assignee: CL Pharma Aktiengesellschaft, Linz, Austria

[21] Appl. No.: 142,677

[22] Filed: Jan. 11, 1988

[30] Foreign Application Priority Data

Jan. 28, 1987 [AT] Austria .................................... 164/87

[51] Int. Cl.$^4$ .................... C07D 413/14; A61K 31/42
[52] U.S. Cl. ................................. 548/238; 514/374
[58] Field of Search ................. 548/238; 514/365, 374

[56] References Cited

FOREIGN PATENT DOCUMENTS 137242  4/1985  European Pat. Off. ............ 548/238

OTHER PUBLICATIONS

Diana et al., Chem Abst., 103:196028(c) (1985).

Primary Examiner—Mary C. Lee
Assistant Examiner—Mary Sue Howard
Attorney, Agent, or Firm—Wenderoth, Lind & Ponack

[57] ABSTRACT

Substituted isoxazoles of the formula

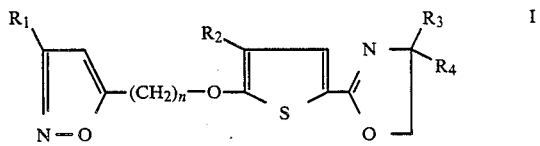

in which $R_1$ denotes $C_1$–$C_4$ alkyl, $R_2$ denotes hydrogen, $C_1$–$C_4$ alkyl chlorine or bromine, $R_3$ and $R_4$, which are the same or different are hydrogen or $C_1$–$C_4$ alkyl, but not both hydrogen and n denotes the interger 6, 7, or 8. The novel compounds have a pronounced antiviral action and can be employed for the treatment and prophylaxis of virus diseases.

5 Claims, No Drawings

ISOXAZOLE DERIVATIVES WITH ANTIVIRAL ACTIVITIES AND PHARMACEUTICAL PRODUCTS CONTAINING THESE

The invention relates to novel substituted isoxazoles of the formula

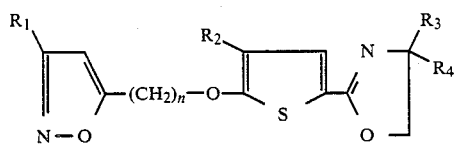

in which
$R_1$ denotes $C_1$-$C_4$ alkyl, $R_2$ denotes hydrogen, $C_1$-$C_4$ alkyl, chlorine or bromine, $R_3$ and $R_4$, which are the same or different are hydrogen or $C_1$-$C_4$ alkyl, but not both hydrogen and n denotes the interger 6, 7 or 8, and pharmaceutical products containing these compounds and their use.

The compounds of the formula I can have optical centers and could be utilized as racemates or in the form of their optical isomers. This invention embraces both the racemates and the optical isomers.

The expression "$C_1$-$C_4$ alkyl" used in this description means straight-chain or branced hydrocarbon groups with 1 to 4 carbon atoms, such as, for example, methyl, ethyl, propyl, isopropyl, butyl or tert.-butyl.

In a preferred group of compounds of the formula I, $R_1$ denotes methyl or ethyl, methyl being particularly preferred. $R_2$ is preferably hydrogen and n preferably represents the number 7.

$R_3$ and $R_4$ are preferably hydrogen or methyl, but both radicals must not be hydrogen.

Particularly preferred individual compounds are 5-(7-(5-(4,5-dihydro-4,4-dimethyl-2-oxazolyl)-2-thienyl)oxyheptyl)-3-methyl-isoxazole and 5-(7-(5-(4,5-dihydro-4-methyl-2-oxazolyl)-2-thienyl)oxyheptyl)-3-methyl-isoxazole.

The isoxazole derivatives of the formula I can be prepared according to the invention by cyclizing a compound of the formula

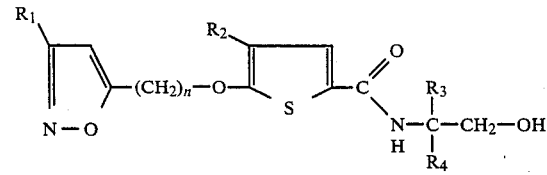

in which $R_1$, $R_2$, $R_3$, $R_4$ and n are as defined above, by treatment with a dehydrating reagent, to form the oxazole ring.

The reaction according to the invention can be carried out in the presence or absence of an inert organic solvent.

If the reaction is carried out in the presence of a solvent, examples of suitable solvents are hydrocarbons, such as benzene, toluene or xylene, halogenated hydrocarbons, such as chloroform, chlorobenzene, methylene chloride or carbon tetrachloride, ethers, such as dioxane, tetrahydrofuran, dimethylformamide and the like, or mixtures of such solvents. Possible dehydrating agents here are the reagents usually employed for such cyclization reactions, for example phosphorus oxychloride, phosphorus pentachloride, thionyl chloride and the like. The dehydrating reagent can be employed for this in equivalent amounts or in a slight excess, for example in amounts of 1.1 to 3 mol per mol of the compound of the formula II. The reaction is carried out at −20° C. to +10° C., preferably at −5° C. to +5° C.

In a particularly preferred embodiment of the process according to the invention, the compounds of the general formula II are in general cyclized in the absence of a separate solvent by treatment with an excess of a liquid dehydrating reagent, which in this case simultaneously serves as the solvent, at −30° C. to +10° C., preferably −5° C. to +5° C. and especially preferably in an icebath at about 0° C. Suitable reagents for this purpose are again phosphorus oxychloride or thionyl chloride, the use of thionyl chloride having proved to be especially advantageous.

The starting compounds of the general formula II used for the process according to the invention can be prepared in a manner which is known per se, starting from known products. In particular, the starting compounds can be synthesized in accordance with the following equation and the specific statements in the examples.

Equation

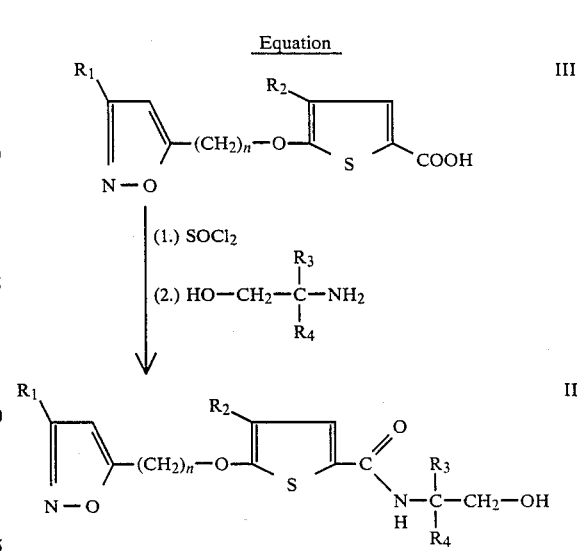

The compounds of the general formula I have an anti-infective action, and in particular a pronounced antiviral action. These useful pharmacological properties can be determined in vitro and in vivo using standard methods. The compounds of the general formula I thereby exhibit an outstanding action in particular against various types of retroviruses, as for example picornaviruses and HIV-viruses. Examples for picornaviruses are rhino- and enteroviruses, which contain echo-, coxackie- and polioviruses. The compounds of the general formula I can therefore be employed in the treatment and prophylaxis of diseases, caused by retroviruses, in mamals, expecially in humans.

The following test methods were used to investigate the anti-viral properties:

A: General Test Against Different Viruses

Serial three-fold dilutions of solutions of the substances under investigation in MEM (minimum essential medium) were prepared in microtiter plates with a flat bottom. The same volumes of the particular virus dilutions in MEM and cell suspension in MEM with 15%

FCS (fetal calf blood serum) were added. The cell concentration here was chosen such that a confluent cell lawn was formed after 1-2 days. The virus dilutions were adjusted so that a complete cytopathic effect occurred after 3-4 days, without the addition of an inhibiting substance.

As controls, cells (cell control), cells with virus (virus control) and cells with the test substances in various concentrations (toxicity control) were also run. The substance concentration at which a cell density which was still lower than in the cell control was observed was determined as the minimum toxic concentration (MTC).

The test substances were dissolved in dimethylsulfoxide and the solutions were diluted in MEM and suspended thoroughly by means of ultrasound.

The compounds according to the invention were investigated for their antiviral action in a representative cross-section of retroviruses and the minimum inhibitory concentration (MIC in ug/ml) was thereby determined.

B: Test Against HIV-Viruses

The anti-HIV assay for testing the anti-AIDS-activity was performed according to Mitsuya, H. et al., Rapid in vitro systems for assessing activity of agents against HTLV-III/LAV, in AIDS: Modern Concepts and Chemotherapeutic Challenges (S. Broder, ed.). Marcel Dekker, Inc., New York, 303-333 (1986):

Human T-lymphocyte-ATH8-cells were pretreated with polybrene at 2 ug/ml for 30 min at 37° C. Cells were then pelleted, suspended in fresh RPMI-1640 culture medium containing 13% fetal calf serum, 11% interleukin-2 (v/v), 50 uM β-mercaptoethanol, 4 mM L-glutamine, 50 units/ml penicillin, and 50 ug/ml streptomycin, and infected with $2\times10^3$ virions/cell for 60-90 min at 37° C. (The HTLV-III$_B$ viruses were derived from a pool of American patients with AIDS. Approximately $6\times10^{10}$ virus particles/ml were obtained from the culture supernatant of HIV-producing H9 cells as described by Mitsuya, H. et al., Proc. Natl. Acad. Sci. USA 82, 7096-7100 (1985).)

This virus concentration represents 400 times the minimum dose required to induce cytopathogenicity in ATH8 cells and, thus, represents a very high multiplicity in infection. After infection, cells were reconstituted in culture medium and seeded in culture tubes at 2 ml/tube in the presence or absence of the test compound. After incubation for 6-7 or 10 days at 37° C., the number of viable cells was counted and compared to controls without the test compound.

In both tests, the compounds of the present invention showed a several times higher activity than the compounds of EP-A 211 157.

The compounds of the general formula I can be administered by a variety of conventional routes, as for example orally and parenterally. Preferably, the compounds are administered orally. In the case of oral administration the daily dose is approximately between 0,005 and 0,5 mg/kg body weight, preferably, between 0,05 and 0,5 mg/kg body weight. However, at the discretion of the attending physician, some variation in dosage can occur, depending upon the condition of the subject being treated, the particular compound employed, and the type of formulation used.

The dosage will be about the same for the treatment of virus diseases and for prophylaxis purposes. For prophylaxis purposes, oral administration is preferred.

The compounds of the general formula I can be used alone or in combination with other pharmaceutically active compounds. In any case, the active ingredient(s) will generally be further combined with pharmaceutically acceptable carriers or diluents. For oral use, suitable pharmaceutical carriers include inert diluents or fillers, thereby forming dosage forms such as tablets, powders, capsules, and the like. These pharmaceutical compositions can, if desired, contain additional ingredients such as flavorings, binders, excipients and the like. For example, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weiht polyethylene glycols.

For parenteral adiministration, solution or suspension of the compounds of formula I in aqueous solutions, for example aqueous propylene glycol, sodium chloride, dextrose or sodium bicarbonate solutions are employed. Such dosage forms are suitably buffered if desired. If appropriate, they are sterilized and contain auxiliaries such as preservatives, stabilizers or emulsifiers and the like.

EXAMPLE 1

5-[7-[5-(4,5-Dihydro-4,4-dimethyl-2-oxazolyl)-2-thienyl]-oxyheptyl]-3-methylisoxazole 0.85 g (2.2 mmol) of N-(2-hydroxy-1,1-dimethylethyl)-5-[7-(3-methyl-5-isoxazolyl)heptyloxy]—2-thiophenecarboxamide are (sic) introduced into 5 ml of thionyl chloride at room temperature and the mixture is stirred for a further 20 minutes. It is then evaporated carefully and the residue is partitioned between 20 ml of saturated sodium bicarbonate solution and 30 ml of ethyl acetate. The aqueous phase is extracted twice more with 30 ml of ethyl aceate each time. The combined organic phases are dried over sodium sulphate, filtered and evaporated.

Yield: 0.7 g of brownish oil (87.5% of theory) The crude product is purified by column chromatography (silica gel 60, eluent: ethyl acetate/petroleum ether=1.1).

Yield: 320 mg of a colorless oil, which crystallizes in the deep-freeze cabinet.

$^1$H-NMR (CDCl$_3$): δ(ppm)=7.28; 7.24; 6.18; 6.13 (AB, 2H, Th-H$_3$, Th-H$_4$); 5.80 (s, 1H, isox-H$_4$); 4.05 (t, 2H, O-CH$_2$); 4.05 (s, 2H, oxaz-CH$_2$); 2.25 (t, 2H, isox-CH$_2$); 1.35 (s, 3H, isox-CH$_3$); 1.09−1.16 (m, 10H, CH$_2$); 1.10 (s, 6H, 2 CH$_3$).

The starting material can be prepared as follows:
N-(2-Hydroxy-1,1-dimethyl-ethyl)-5-[7-(3-methyl-5-isoxazolyl)heptyloxy]-2-thiophenecarboxamide 1.0 g (3.1 mmol) of 5-[7-(3-methyl-5-isoxazolyl)-heptyloxy]-2-thiophenecarboxylic acid are stirred into 10 ml of thionyl chloride at 0° C. The mixture is stirred at this temperature for a further 20 minutes and excess thionyl chloride is distilled off in vacuo at a bath temperature of 30° C. The residue is freed from thionyl chloride residues in vacuo and dissolved in 7 ml of absolute methylene chloride. This solution is added dropwise with stirring (sic) to a solution of 0.61 g (6.8 mmol) of 2-amino-2-methyl-1-propanol in 7 ml of absolute methylene chloride in the course of 40 minutes at a temperature between 0 and 5° C., with stirring. The mixture is allowed to warm to room temperature and is stirred for a further hour. The reaction mixture is then poured onto 10 ml of 2N HCl, the phases are separated and the aqueous phase is extracted twice more than 30 ml of methylene chloride each time. The combined organic phases are washed with 10 ml of water, dried over sodium sulphate, filtered and evaporated.

Yield: 1.1 g of brownish crystals (90.2% of theory).
Melting point: 73°–75° C. (acetonitrile).

EXAMPLE 2

R,S-5-[7-[5-(4,5-Dihydro-4-methyl-2-oxazolyl)-2-thienyl]-oxyheptyl]-3-methylisoxazole 0.42 g (1.1 mmol) of R,S-N-(2-hydroxy-1-methyl-ethyl)-5-[7-(3-methyl-5-isoxazolyl)heptyloxy]-2-thiophenecarboxamide are (sic) introduced into 5 ml of thionyl chloride at room temperature and the mixture is stirred for a further 20 minutes. It is then evaporated carefully and the residue is partitioned between 20 ml of saturated sodium bicarbonate solution and 30 ml of ethyl acetate. The aqueous phase is extracted twice more with 30 ml of ethyl acetate each time. The combined organic phases are dried over sodium sulphate, filtered and evaporated.

Yield: 0.39 g of brownish oil (97.5% of theory).

The crude product is purified by column chromatography (silica gel 60, eluent: ethyl acetate/petroleum ether =1:1).

Yield: 120 mg of colorless crystals.
Melting point: 43.5°14 45° C. (diisopropyl ether).

The starting material can be prepared as follows: R,S-N-(2-Hydroxy-1-methyl-ethyl)-5-[7-(3-methyl-5-isoxazolyl)heptyloxy]-2-thiophenecarboxamide.

0.5 g (1.5 mmol) of 5-[7-(3-methyl-5-isoxazolyl)-heptyloxy]-2-thiophenecarboxylic acid are (sic) stirred into 6 ml of thionyl chloride at 0° C. The mixture is stirred at this temperature for a further 20 minutes and excess thionyl chloride is distilled off in vacuo at a bath temperature of 30° C. The residue is freed from thionyl chloride residues in vacuo and dissolved in 4 ml of absolute methylene chloride. This solution is added dropwise with stirring (sic) to a solution of 0.26 g (3.4 mmol) of R,S-2-amino-1-propanol in 4 ml of absolute methylene chloride in the course of 40 minutes at a temperature between −10° and −15° C., with stirring. The mixture is allowed to warm to room temperature and is stirred for a further hour. The reaction mixture is then poured onto 10 ml of 2N HCl, the phases are separated and the aqueous phase is extracted twice more with 30 ml of methylene chloride each time. The combined organic phases are washed with 10 ml of water, dried over sodium sulphate, filtered and evaporated.

Yield: 0.49 g of brownish crystals (83.3% of theory).
Melting point: 84°–86° C. (acetonitrile).

EXAMPLE 3

S-5-[7-[5-(4,5-Dihydro-4-methyl-2-oxazolyl)-2-thienyl]-oxyheptyl]-3-methylisoxazole 1.1 g (2.9 mmol) of S-N-(2-hydroxy-1-methyl-ethyl)-5-[7-(3-methyl-5-isoxazolyl)heptyloxy]-2-thiophenecarboxamide are introduced into 15 ml of thionyl chloride at room temperature and the mixture is stirred for a further 20 minutes. It is then evaporated carefully and the residue is partitioned between 20 ml of saturated sodium bicarbonate solution and 30 ml of ethyl acetate. The aqueous phase is extracted twice more with 30 ml of ethyl acetate each time. The combined organic phases are dried over sodium sulphate, filtered and evaporated.

Yield: 0.96 g of brownish crystals (91.6% of theory).
The crude product is recrystallized from diisopropyl ether.
Melting point: 53°–55° C. (diisopropyl ether).

The starting material can be prepared as follows: S-N-(2-Hydroxy-1-methyl-ethyl)-5-[7-(3-methyl-5-isoxazolyl)heptyloxy]-2-thiophenecarboxamide.

1.1 g (3.4 mmol) of 5-[7-(3-methyl-5-isoxazolyl)-heptyloxy]-2-thiophenecarboxylic acid are stirred into 10 ml of thionyl chloride at 0° C. The mixture is stirred at this temperature for a further 20 minutes and excess thionyl chloride is distilled off in vacuo at a bath temperature of 30° C. The residue is freed from thionyl chloride residues in vacuo and dissolved in 10 ml of absolute methylene chloride. This solution is added dropwise with stirring (sic) to a solution of 0.57 g (7.6 mmol) of S-2-amino-1-propanol in 10 ml of absolute methylene chloride in the course of 40 minutes at a temperature between −10° and −15° C., with stirring. The mixture is allowed to warm to room temperature and is stirred for a further hour. The reaction mixture is then poured onto 20 ml of 2N HCl, the phases are separated and the aqueous phase is extracted twice more with 50 ml of methylene chloride each time. The combined organic phases are washed with 10 ml of water, dried over sodium sulphate, filtered and evaporated.

Yield: 1.2 g of brownish crystals (93.0% of theory).
Melting point: 82°–85° C. (acetonitrile).

What we claim is:

1. A compound of the formula

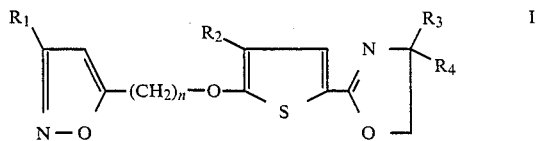

in which
R$_1$ denotes C$_1$–C$_4$ alkyl,
R$_2$ denotes hydrogen, C$_1$–C$_4$ alkyl, chlorine or bromine,
R$_3$ and R$_4$, which are the same or different are hydrogen or C$_1$–C$_4$ alkyl, but not both hydrogen and n denotes the integer 6, 7 or 8.

2. The compound of the formula I as claimed in claim 1, in which R$_1$ denotes methyl, R$_2$ hydrogen and n denotes the integer 7.

3. The compound of the formula I as claimed in claim 1, in which R$_3$ and R$_4$, which are the same or different are hydrogen or methyl, but not both hydrogen.

4. 5-(7-(5-(4,5-dihydro-4,4-dimethyl-2-oxazolyl)-2-thienyl)oxyheptyl)-3-methyl-isoxazole.

5. 5-(7-(5-(4,5-dihydro-4-methyl-2-oxazolyl)-2-thienyl)oxyheptyl)-3-methyl-isoxazole.

* * * * *